United States Patent [19]

Schneider et al.

[11] 4,178,167
[45] Dec. 11, 1979

[54] HERBICIDAL N-(HALOACETYL)-N-(N'-METHYLENEPYR-ROLIDONYL)-2-ALKOXYANILINES USEFUL AS HERBICIDES

[75] Inventors: Louis Schneider, Elizabeth; David E. Graham, Westfield, both of N.J.

[73] Assignee: GAF Corporation, New York, N.Y.

[21] Appl. No.: 892,146

[22] Filed: Mar. 31, 1978

Related U.S. Application Data

[63] Continuation-in-part of Ser. No. 807,066, Jun. 16, 1977, abandoned.

[51] Int. Cl.$^2$ .............................................. A01N 9/22
[52] U.S. Cl. ................................. 71/95; 260/326.43; 260/326.5 J
[58] Field of Search ........................ 260/326.43; 71/95

[56] References Cited
U.S. PATENT DOCUMENTS 3,769,301  10/1973  Olin ................................. 260/326.43

Primary Examiner—Donald G. Daus
Assistant Examiner—Lisa Jones
Attorney, Agent, or Firm—Walter C. Kehm; Walter Katz

[57] ABSTRACT

Herbicidal N-(haloacetyl)-N-(N'-methylenepyrrolidonyl)-2-alkoxyanilines are provided in this invention having the formula:

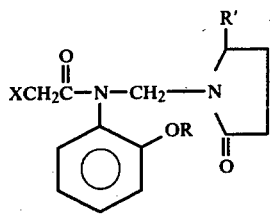

where R is alkyl of 1–6 carbon atoms, R' is hydrogen or lower alkyl of 1–3 carbon atoms, and X is halogen.

Another feature of the invention is the provision of N-(N'-methylenepyrrolidone)-2-alkoxyaniline or intermediates useful in making such herbicides. These intermediates are prepared by reaction of a 2-alkoxyaniline with an N-methylolpyrrolidone or an N-halomethylenepyrrolidone. The herbicide product than is obtained by acylation of the intermediate with a haloacetyl halide.

The compounds of the present invention show good herbicidal activity against grassy weeds.

1 Claim, No Drawings

HERBICIDAL N-(HALOACETYL)-N-(N'-METHYLENEPYRROLIDONYL)-2-ALKOXYANILINES USEFUL AS HERBICIDES

This application is a continuation-in-part of copending application Ser. No. 807,066, filed June 16, 1977, now abandoned.

BACKGROUND OF THE DISCLOSURE

1. Field of the Invention

This invention relates to novel N-(haloacetyl)N-(N'-methylenepyrrolidonyl)-2-alkoxyanilines which are useful as herbicides, and to intermediates useful in the synthesis thereof.

2. Description of the Prior Art

U.S. Pat. Nos. 3,769,301 and 3,907,544 disclose related N-(acyl-tert-amidoalkyl)acetanilides, including N-methylenepyrrolidonyl derivatives; however, these compounds are substituted with 2,6-dialkyl groups only.

SUMMARY OF THE INVENTION

The present invention provides herbicidal N-(haloacetyl)-N-(N'-methylenepyrrolidonyl)-2-alkoxyanilines having the formula:

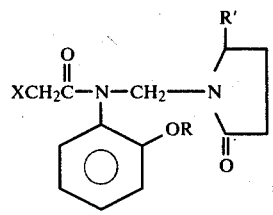

where R is alkyl of 1–6 carbon atoms, R' is hydrogen or lower alkyl of 1–3 carbon atoms, X is halogen.

Another feature of the invention is the provision of N-(N'-methylenepyrrolidone)-2-alkoxyaniline intermediates useful in making such herbicides. The intermediates are prepared by reaction of a 2-alkoxyaniline with an N-methylolpyrrolidone or an N-halomethylenepyrrolidone. The herbicide product then is obtained by acylation of the intermediate with a haloacetyl halide.

The herbicide compounds of the present invention show excellent herbicidal activity against grassy weeds.

DETAILED DESCRIPTION OF THE INVENTION

The herbicidally active compounds of the present invention are obtained by the following two-step reaction sequence:

STEP 1

Formation of Intermediate Compounds

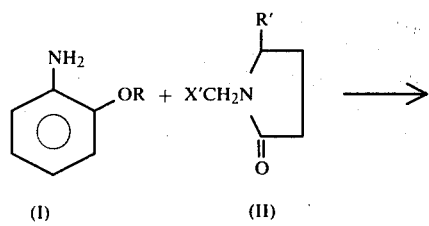

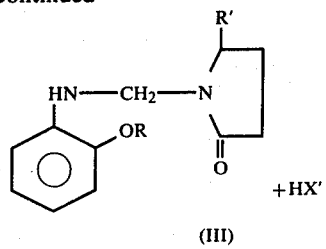

where R is alkyl having from 1-6 carbon atoms, R' is hydrogen or lower alkyl of from 1–3 carbon atoms, and X' is hydroxyl or halogen.

STEP 2

Formation of Herbicide Compounds from Intermediates

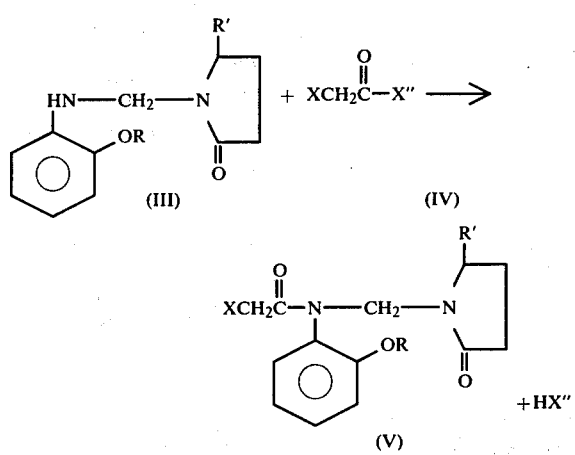

where X and X" are halogen atoms.

Starting material I is an o-alkoxyaniline, which is commercially available for lower alkoxy compounds such as o-methoxyaniline and o-ethoxyaniline. The higher o-alkoxyaniline starting compounds may be prepared from o-nitrophenol by alkylation of the hydroxyl group and reduction of the nitro group. Such a scheme is used for preparing o-propoxyaniline, o-butoxyaniline, sec. butoxyaniline, and other higher o-alkoxyaniline materials.

Starting material II, where X' is hydroxyl, i.e. an N-methylolpyrrolidone, is prepared according to the method described in U.S. Pat. No. 3,073,843 and is a condensation of 2-pyrrolidone or 5-alkyl-2-pyrrolidone, i.e. with paraformaldehyde in basic solution. Compounds in which X' is halogen, an N-halomethylenepyrrolidone, are obtained from N-methylolpyrrolidone by halogenation with such conventional agents as thionyl chloride, as described in Chemical Abstracts 54, 1286f (1960).

In accordance with the invention, useful intermediates in the synthesis of the herbicides herein are prepared in Step 1 by condensing the 2-alkoxyaniline with N-methylolpyrrolidone or N-halomethylene pyrrolidone. These intermediates are N-(N'-methylenepyrrolidonyl)-2-alkoxyanilines, and are isolated from solution in the reaction sequence.

In Step 2, thereafter, the intermediate is acylated with a haloacetyl halide IV to provide the desired N-haloacetyl-N-(N'-methylenepyrrolidonyl)-2-alkoxyaniline product V.

When N-methylolpyrrolidone is used in Step 1, the condensation reaction to form the intermediate is carried out by refluxing a 2-alkoxyaniline with N-methylolpyrrolidone under azeotropic conditions in a suitable solvent, while removing the stoichiometric amount of water from the reaction mixture.

In the alternative method of Step 1 using N-halomethylenepyrrolidone as the condensing reactant, the condensation may be carried out under milder temperature conditions than with N-methylolpyrrolidone. Accordingly, it is a preferred reactant for intermediates which may be sensitive to heat.

As used herein the term "alkyl" includes both straight and branched chain hydrocarbons. The term "halogen" includes chloro, bromo and iodo.

The compounds of this invention are especially useful as agricultural herbicides. They show particularly effective herbicidal activity against Japanese millet, foxtail millet and crabgrass.

Usually they are applied to the soil at the rate of about 1 to 25 lbs. per acre or as a foliar spray on the weeds at concentrations of about 30 to 260 ppm., depending on various circumstances of the susceptibility of the weed to the herbicide, the weather, the stage of growth and various other factors. The material also may be applied as a dust. As a dust, it is practical to extend it with diluents, such as bentonite, chalk, clay, diatomaceous earth, fullers earth, mica, ground slate or any of the other usual carriers for agricultural chemicals.

As a spray, it may be incorporated into water as a solution. The higher molecular weight compounds may be dissolved first in a solvent, such as an alcohol, or a petroleum fraction, such as isoparaffinic hydrocarbons, naphtha or kerosene, which may be dissolved in a suitable solvent and fogged or sprayed without water. Usually it is desirable to incorporate emulsifying agents and other wetting agents to insure complete contact with the weed.

Following are examples of preparation of the compounds of the invention and are presented by way of illustration and are not intended to be limiting unless otherwise specified.

EXAMPLE 1

N-(CHLOROACETYL)-N-(N'-METHYLENEPYRROLIDONYL)-2-METHOXYANILINE

N-Methylolpyrrolidone

2-Pyrrolidone (212.4 g., 2.0 mole) and potassium hydroxide (0.6 g) is heated to 80° C. and paraformaldehyde (75.6 g, 2.6 mole) are added during 10 minutes, and the mixture maintained at 75°–80° C. for ½ hr. The desired product then is crystallized from 1 part of benzene to yield 227 g. (88.2%), m.p. 78°–80° C. of product.

N-(N'-Methylenepyrrolidonyl)-2-Methoxyaniline

2-Methoxyaniline (24.6 g., 0.2 mole), xylene (100 cc), N-methylolpyrrolidone (23.0 g., 0.2 mole) are refluxed under azeotropic conditions until the stoichiometric amount of water is removed. The product is crystallized from xylene-ether, and vacuum dried, to yield 172 g. (89%), m.p. 106°–108° C. of product.

Anal. Calcd for $C_{12}H_{16}N_2O_3$: N, 12.72 Found: N, 12.98.

N-(Chloroacetyl)-N-(N'-Methylenepyrrolidonyl)-2-Methoxyaniline

N-Methylenepyrrolidonyl-2-methoxyaniline (14.0 g., 0.047 mole), benzene (75 cc) and N,N-diisopropylethylamine (6.7 g., 0.051 mole) are cooled to 5° C., and chloroacetyl chloride (5.9 g., 0.052 mole) in benzene (10 cc) is added during 1 hr. The reaction mixture is stirred at 0°–5° C. for 3 hrs., stirred overnight at ambient temperature, washed with 100 cc of cold water, 150 cc of 10% potassium bicarbonate, 150 cc of 5% hydrochloric acid, and finally 100 cc of water. The benzene is removed by rotoevaporation and the desired product is crystallized from ether, to yield 6.0 g. (43.2) m.p. 110°–111° C. of product.

Anal. Calcd for $C_{14}H_{17}ClN_2O_3$: Cl, 11.95; N, 9.44 Found: Cl, 11.76; N, 9.23.

EXAMPLE 2

N-(CHLOROACETYL)-N-(N'-METHYLENEPYRROLIDONYL)-2-ETHOXYANILINE

N-Methylenepyrrolidonyl-2-ethoxyaniline (11.7 g., 0.050 mole), prepared according to the procedure of Example 1, dichloromethane (60 cc) and N,N-diisopropylethylamine (7.1 g., 0.055 mole) are cooled to 5° C., and chloroacetyl chloride (6.2 g., 0.055 mole) in dichloromethane (25 cc) is added during one hr. The reaction mixture is stirred at 0°–5° C. for 3 hrs., stirred overnight at ambient temperature, washed with 100 cc of cold water, 150 cc of 10% potassium bicarbonate, 150 cc of 5% hydrochloric acid, and finally 100 cc of water. The dichloromethane is removed by rotoevaporation and the desired product crystallized from methanol to yield 5.0 g. (32.3%), m.p. 92°–94° C.

Anal. Calcd for $C_{15}H_{19}ClN_2O_3$: Cl, 11.41; N, 9.02 Found: Cl, 11.37; N, 8.89.

EXAMPLE 3

N-(CHLOROACETYL)-N-(N'-METHYLENEPYRROLIDONDYL)-2-PROPOXYANILINE o-Propoxynitrobenzene o-Nitrophenol (111.2 g., 0.8 mole), 1-bromopropane (98.4 g., 0.8 mole), anhydrous potassium carbonate (121.4 g., 0.88 mole) and any acetone (800 cc) are refluxed for 70 hrs., filtered the reaction mass, the residue was washed with acetone, and the filtrate rotoevaporated. To the residue of the evaporation was added 200 cc of dichloromethane and rotoevaporated again; the residue was washed with 100 cc of water and separated into two layers. The dichloromethane layer was washed with 100 cc of 10% $Na_2CO_3$, separated again, washed again with 100 cc of water, and the dichloromethane layer was fractionated under vaccum. The main fraction distilled at 103°–106° C. at 0.2–0.3 mm Hg., giving 130 g. of product (87% yield).

o-Propoxyaniline

Iron 60 mesh (134.5 g., 2.40 mole), concentrated HCl (37.4 cc), ethanol (630 cc), and water (570 cc) are stirred under nitrogen and the temperature of the mixture is raised to reflux. Then o-propoxynitrobenzene (12.5 g., 0.69 mole), is added at reflux over a period of 5 hrs. and refluxed for 3–4 hrs. Then the mixture is neutralized with concentrated ammonia to a pH of 8–9. The temperature is raised to 30° C., and the reaction mass filtered, 200 cc ether added, the organic layer separated.

The product distilled at vapor temperature of 65°-67° C. at 0.05-0.03 mm. yielding 77 g of product (74%).

N-Chloromethylenepyrrolidone

N-Methylolpyrrolidone (225 g., 1.95 mole) and toluene (400 cc) were chilled at 5° C. with stirring and thionyl chloride (257 ml., 3.3 mole) in toluene (300 cc) was added dropwise in 2 hrs. and the mixture allowed to remain overnight. The toluene solvent then was rotoevaporated and the residue distilled at 107°-110° C. at 2.5-3 mm. Hg. yielding 151.5 g (58.2%) of product which crystallized on standing, m.p. 35°-37° C.

N-Methylenepyrrolidonyl-2-Propoxyaniline o-Propoxyaniline (10 g., 0.07 mole) sodium carbonate (7.0 g.) and toluene (60 ml) were chilled to 5° C. with stirring and N-chloromethylene pyrrolidone (8.8 g., 0.07 mole) in toluene (40 cc) was added dropwise during ½ hr. and allowed to stand overnight. Then 100 ml water was added to the mixture; the toluene layer was filtered, and rotoevaporated to give 14.4 g of crude product which was recrystallized from methanol yielding 9.0 g. of product (54.8%), m.p. 83°-84° C.

N-Chloroacetyl-N-(N'-Methylenepyrrolidonyl)-2-Propoxyaniline

N-Methylenepyrrolidonyl-2-propoxyaniline (7 g., 0.03 mole), sodium carbonate (3 g.) and toluene (100 cc) was added with stirring chloroacetyl chloride (3.2 g., 2.2 ml), and the reaction continued overnight. The reaction mixture was washed free of salts with 100 cc of water and the toluene layer filtered rotoevaporated and crystallized from methanol to provide 5.6 g. of crystalline product (61.5% yield) m.p. 91°-92° C.

EXAMPLE 4

N-(CHLOROACETYL)-N-(N'-METHYLENEPYRROLIDONYL)-2-BUTOXYANILINE

N-(N'-Methylenepyrrolidonyl)-2-Butoxyaniline

A mixture of o-butoxyaniline (79.0 g., 0.48 mole), prepared according to the procedure described in Example 3, N-methylolpyrrolidone (55.2 g., 0.48 mole) and toluene (194 cc) are refluxed under azeotropic conditions at 118° C. until the stoichiometric amount of water is removed (7 cc). The product is crystallized from toluene-hexane, and vacuum dried to provide 31 g. of product (24.7% yield).

N-(Chloroacetyl)-N-(N'-Methylenepyrrolidonyl)-2-Butoxyaniline

A mixture of N-methylenepyrrolidonyl-2-butoxyaniline (5 g., 0.02 mole), sodium carbonate (1.8 g., 0.02 mole) and toluene (50 cc) were cooled to 0.5° C., and a solution of chloroacetyl chloride (2 g., 0.02 mole) in 200 cc toluene was added over 1 hr. at 0°-5° C. The reaction mixture was allowed to warm to room temperature, and 100 cc of water was added to form two layers. The toluene layer was separated, dried over magnesium sulfate, rotoevaporated yielding 6.1 g. (93.8%) of a viscous oil product.

EXAMPLE 5

N-(CHLOROACETYL)-N-(N'-METHYLENEPYRROLIDONYL)-2-SEC-BUTOXYANILINE

N-(N'-Methylenepyrrolidonyl)-2-sec-Butoxyaniline

A mixture of o-sec-butoxyaniline (32 g., 0.19 mole), N-methylolpyrrolidone (21.9 g., 0.19 mole), and xylene (100 ml) were refluxed under azeotropic conditions for about 1¾ hrs. and about 2 ml. of water was collected. The xylene solution was washed with 5% hydrochloric acid followed by three water washes. The xylene layer was dried over magnesium sulfate and the solvent removed by rotoevaporation yielding 46.5 g (97.8%) product.

N-Chloroacetyl-N-(N'-Methylenepyrrolidonyl)-2-sec-Butoxyaniline

The product of Example 5 was acylated with chloroacetyl chloride according to the procedure outlined in Example 4 yielding 4.9 g (98.2%) of the corresponding sec-butoxyaniline compound.

EXAMPLE 6

N-(CHLOROACETYL)-N-(N'-METHYLENE-5-METHYL-2-PYRROLIDONYL)-2-ETHOXYANILINE

N-(N'-Methylene-5-Methyl-2-Pyrrolidonyl)-2-Ethoxyaniline

A mixture of N-methylol-5-methyl-2-pyrrolidonyl (25.8 g., 0.20 moles), o-ethoxyaniline (27.5 g., 0.20 moles), and xylene (81 ml.) were refluxed for 1 hr. while removing water; then an additional 25 ml. of xylene was added and refluxing continued for an additional 3 hrs. The xylene was removed by rotoevaporation and the residue crystallized on standing. Recrystallized from methanol provided 25.9 g. of product (52.1% yield) m.p. 89°-91° C.

N-Chloroacetyl-N-(N'-Methylene-5-Methyl-2-Pyrrolidonyl)-2-Ethoxyaniline

The product of Example 6 was acylated with chloroacetyl chloride according to the procedure outlined in Example 4 yielding 3.0 g. (43.4%) m.p. 80°-81° C.

EXAMPLE 7

Herbicidal Tests

Primary tests on the compounds of Examples 1–6 were made on two flats seeded with six species of representative monocotyledonous and dicotyledonous plants (Japanese millet, foxtail millet and crabgrass). The test chemical was applied to one such flat immediately after it was seeded. The other flat contained plants on which the first true leaves had developed. Both of these flats were sprayed, simultaneously, with the test chemical at 2080 ppm, a rate sufficient to give 10 lb/acre (104 mg in 50 ml of water on 144 square inches). Diuron, 3-(3,4-dichlorophenyl)-1,1-dimethylurea, as a standard, was applied pre-emergence at the rate of 2.5 lb/acre. The response was rated 12 to 21 days after treatment on a scale of 0 to 10 where 0 represents no injury and 10 represents complete kill.

Table I

| | Pre-Emergence Primary Herbicidal Ratings | | | | | | |
|---|---|---|---|---|---|---|---|
| | Example No. | | | | | | Standard |
| Test Plant | 1 | 2 | 3 | 4 | 5 | 6 | Diuron |
| | Ratings | | | | | | |
| Japanese Millet | 10 | 10 | 9 | 9 | 8 | 10 | 10 |
| Crabgrass | 9 | 10 | 9 | 9 | 10 | 10 | 10 |
| Foxtail Millet | 9 | 10 | 8 | 8 | 8 | 9 | 10 |

Secondary tests were made on the above Examples 1–6 at lower concentrations, namely, at 5 lbs/acre, against commercial Lasso as the standard.

Table II
Pre-Emergence Secondary Herbicidal Ratings

| Test Plant | 1 | 2 | 3 | 4 | 5 | 6 | Standard Lasso |
|---|---|---|---|---|---|---|---|
| | | | | Ratings | | | |
| Japanese Millet | 9 | 10 | 10 | 10 | 9 | 10 | 10 |
| Crabgrass | 4 | 10 | 10 | 10 | 9 | 10 | 10 |
| Foxtail Millet | 8 | 10 | 8 | 8 | 8 | 8 | 10 |

The tests demonstrate the effectiveness of the compounds of the invention against grassy weeds.

While the invention has been described with particular reference to certain embodiments thereof, it will be understood that certain modifications and changes may be made which are within the skill of the art. Therefore it is intended to be bound only by the appended claims.

What is claimed is:

1. A method of controlling grassy weeds which consists essentially of applying thereto a herbicidally effective amount of N-haloacetyl-N-(N'-methylenepyrrolidonyl)-2-alkoxyaniline compounds of the formula:

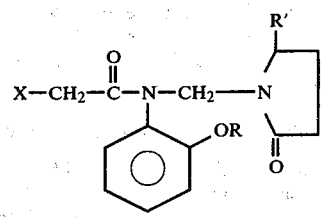

where R is alkyl of 1–6 carbon atoms, R' is hydrogen or lower alkyl of 1–3 carbon atoms, and X is chloro, bromo or iodo.

* * * * *